(12) United States Patent
Transfiguracion et al.

(10) Patent No.: US 7,754,421 B2
(45) Date of Patent: Jul. 13, 2010

(54) DETECTION OF INTACT RECOMBINANT VIRUSES

(75) Inventors: Julia Transfiguracion, Dollard-des-Ormeaux (CA); Amine Kamen, Montréal (CA)

(73) Assignee: National Research Council of Canada, Ontario (CA)

( * ) Notice: Subject to any disclaimer, the term of this patent is extended or adjusted under 35 U.S.C. 154(b) by 277 days.

(21) Appl. No.: 11/661,932

(22) PCT Filed: Nov. 18, 2005

(86) PCT No.: PCT/CA2005/001763

§ 371 (c)(1),
(2), (4) Date: Aug. 20, 2007

(87) PCT Pub. No.: WO2006/053443

PCT Pub. Date: May 26, 2006

(65) Prior Publication Data

US 2008/0113336 A1    May 15, 2008

Related U.S. Application Data

(60) Provisional application No. 60/628,908, filed on Nov. 19, 2004.

(51) Int. Cl.
*C12Q 1/70* (2006.01)
*C12Q 1/68* (2006.01)
*G01N 30/96* (2006.01)
*C12N 7/02* (2006.01)

(52) U.S. Cl. .............................. 435/5; 435/6; 435/239; 422/69

(58) Field of Classification Search ....................... None
See application file for complete search history.

(56) References Cited

OTHER PUBLICATIONS

Tan, et al. Detection of duck hepatitis B virus DNA fragments using on-column intercalating dye labeling with capillary electrophoresis—laser-induced fluorescence. Journal of Chromatography A. 1999; 853:309-319.*
Gao, et al. Purification of Recombinant Adeno-Associated Virus Vectors by Column Chromatography and Its Performance in Vivo. Human Gene Therapy. 2000; 11:2079-2091.*
Hasan, et al. Versatility of the Accessory C Proteins of Sendai Virus: Contribution to Virus Assembly as an Additional Role. Journal Of Virology. 2000; 74(12):5619-5628.*
Skeidsvoll and Ueland (Analysis of Double-Stranded DNA by Capillary Electrophoresis with Laser-Induced Fluorescence Detection Using the Monomeric Dye SYBR Green I. Analytical Biochemistry. 1995; 231:359-365.*

* cited by examiner

*Primary Examiner*—Mary E Mosher
*Assistant Examiner*—Stuart W Snyder
(74) *Attorney, Agent, or Firm*—Ogilvy Renault LLP

(57) ABSTRACT

In accordance with the present invention, there is provided a new method for detection and quantification of virus and viral particles, comprising the step of labeling the nucleic acids of an intact virus or viral particle with a dye that emits fluorescence once complexed with the nucleic acids and detecting the virus or viral particle with a chromatograph equipped with a fluorescence detector.

24 Claims, 11 Drawing Sheets

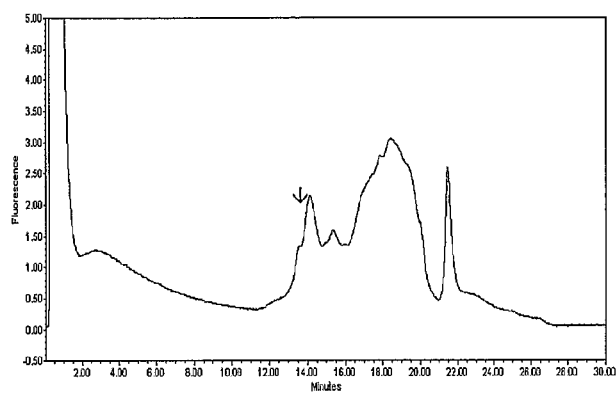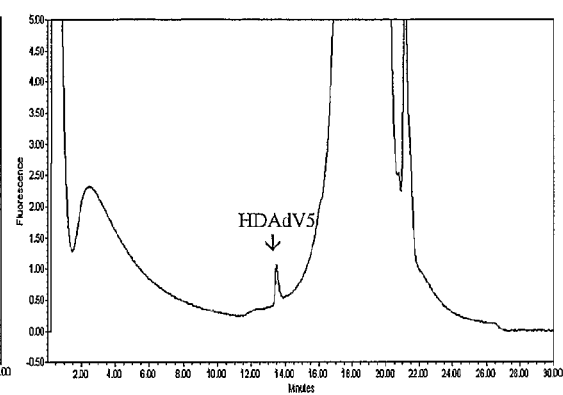
Fig. 10A                    Fig. 10B

DETECTION OF INTACT RECOMBINANT VIRUSES

CROSS-REFERENCE TO RELATED APPLICATIONS

This application claims priority on U.S. provisional application Ser. No. 60/628,908 filed Nov. 19, 2004, the entire content of which is hereby incorporated by reference.

TECHNICAL FIELD

The present invention relates to a new method for detecting and quantifying viruses or viral particles in a sample.

BACKGROUND OF THE INVENTION

Viral vectors are the most popular gene delivery vehicles in gene therapy studies to treat various kinds of cancer, monogenic, vascular and infectious diseases such as cystic fibrosis, coronary heart disease and acquired immune deficiency syndrome (AIDS). Over the last fifteen years, the use of viral vectors in human gene therapy clinical trials have increased tremendously comprising 70% of the total clinical trials conducted worldwide. Murine-derived retroviral vectors (RV) are the most commonly used vectors (27%) followed by adenovirus (AdV) (26%), pox virus (7.2%), vaccinia virus (4.7%), herpes simplex virus (3%) and adeno-associated virus (AAV) (2.5%). For RV, the primary reason for being attractive gene delivery vehicles are their ability to integrate efficiently into the host genome maintaining a long-term gene expression while for AdV is their ease of production at high titers. The helper dependent adeno-associated virus (AAV) is one promising vector primarily because it is non-pathogenic and has a wide variety of host range. Likewise, a helper dependent adenovirus (HDAdV) that is fully deleted of its viral genes and requires a helper (as the term implies) virus for replication has also been commonly used mainly because of safety as it is less immunogenic than the first generation adenovirus. And for the purpose of covering the scope of this work, an emerging virus that have shown potential as gene delivery vector efficiently transducing mammalian cells is the insect cell derived baculovirus (BV) carrying mammalian cell promoters commonly termed as "BacMam". BV has advantages over the other vectors since they are able to accommodate large foreign genes, are produced at high titers and non-pathogenic. The use of viral vectors in gene therapy continues to hold promise for the future despite major setbacks that only motivated for the development of safer vector constructs and new production systems to obtain higher virus titers. A great deal of effort has also been dedicated to the advancement of manufacturing processes whereby physical methods to quantify viral particles played a major role. These methods allowed results to be obtained in a matter of minutes facilitating process development in complementary to the traditional titration assays for infectious particles assays taking several days before a result is obtained. Several of these assays currently used for the quantification of total vector particles are ion-exchange high performance liquid chromatography (IE-HPLC) [Shabram P W, et al., *Hum Gene Ther.* 1997; 8: 453-465; Klyushnichenko V, et al. *J Chromatogr B Biomed Sci Appl.* 2001; 755: 27-36; Transfiguracion J, et al., *J Chromatogr B Analyt Technol Biomed Life Sci.* 2004; 813: 167-173; and Debelak D, et al., *J Chromatogr B Biomed Sci Appl.* 2000; 740: 195-202]; absorbance at 260 nm ($Abs_{260nm}$) in the presence of SDS [Maizel J V Jr, et al., *Virology.* 1968; 36: 126-36; and Maizel J V Jr, et al., *Virology.* 1968; 36: 126-36]; viral genome labeling upon viral destruction [Murakami P, McCaman M T. *Anal Biochem.* 1999; 274: 283-8]; enzyme linked immunosorbent assay (ELISA) [Grimm D, et al. *Gene Ther.* 1999; 6: 1322-1330]; dot blot assay [Drittanti L, et al., *Gene Ther.* 2000; 7: 924-929] and polymerase chain reaction (PCR) [Sanburn N, Cornetta K. *Gene Ther.* 1999; 6: 1340-1345; Clark K R, et al., *Hum Gene Ther.* 1999; 10: 1031-1039; Carmo M, et al., *J Virol Methods.* 2004; 119: 115-119; Rohr U P, et al., *J Virol Methods.* 2002; 106: 81-88; and Veldwijk M R, et al., *Mol Ther.* 2002; 6: 272-278]. Although these methods provide rapid results, they also have their own disadvantages suffering either from non-specificity, insensitivity, laborious and expensive. For example, $Abs_{260nm}$ and genome labeling upon viral destruction are only applicable in the analysis of highly purified vector preparations devoid of contaminants. The presence of contaminants particularly host residual DNA could result in the overestimation of total particles since they also highly absorbs at $Aba_{260nm}$. Quantification with crude preparations is not possible with these methods since there is no discrimination between the virus and the contaminants. IE-HPLC assays are specific because the virus is efficiently resolved from the rest of the sample components. However, these methods lack sensitivity requiring high virus titers for quantification. It has been reported that the quantification limits (QL) of these methods range from $2.5 \times 10^7$ and $3 \times 10^8$ viral particles per ml (VP/ml) for purified AdV5 and $1 \times 10^8$ VP/ml for virus lysates [Shabram P W, et al., *Hum Gene Ther.* 1997; 8: 453-465; and Transfiguracion J, et al., *J Chromatogr B Biomed Sci Appl.* 2001; 761: 187-194]. ELISA assays are time consuming and expensive, not suitable for the analysis of large volume of samples. PCR assays which are commonly used for the quantification of packaged vector genomes (vg's) are laborious and tend to suffer from non-specificity resulting in high variability of results requiring standardization on the method of operation for the comparison of inter-laboratory results [Veldwijk M R, et al., *Mol Ther.* 2002; 6: 272-278]. The validity of results obtained by this method also raised concerns due to the likeliness of unpackaged genome present in the preparation [Bartlett J S, et al., *J Virol.* 2000; 74: 2777-2785; and Ferrari F K, et al., *J Virol.* 1996; 70: 3227-3234].

Continuous efforts dedicated to the improvement of these methods and the development of new and better assays would only result in the better understanding of these vectors and better manufacturing processes.

Physical methods to quantify viral particles have become useful tools in the development of manufacturing processes of gene therapy vectors. Results can now be obtained in minutes facilitating process development. These methods though useful have their disadvantages suffering either from non-specificity, low sensitivity, laborious and expensive not suitable for routine use.

Accurate quantification of vector particles is critical in the design and execution of a successful pre-clinical and clinical gene therapy trials and experiments. Moreover, quantification assays for viral particles is an inherent and important part of a viral vector manufacturing process starting at the early stages of drug development. It is quite often overlooked at this stage but it is apparent that without a quantification assay, processes cannot be developed further. As previously discussed, particles quantification assays based on the physicochemical characteristics of the virus have contributed to the speedy development of viral manufacturing processes. However, not one of these assays was actually able to fulfil an ideal routine assay that caters to all types of samples along the manufacturing process. For example, MV, RV and HDAdV are currently produced in low titers requiring the need for a more sensitive assay to be able to monitor a production. Crude virus preparations must be analysed with an assay that is able to discriminate the virus from the rest of the sample components or even better from the infectious to the non-infectious particles without compromising sensitivity and specificity. These are but a few examples of the limitations that some of the current methods are facing.

A method that would meet all these limitations would therefore be an ideal quantification assay.

SUMMARY OF THE INVENTION

One aim of the present invention is to provide a method for detecting intact viral particles using a combination of a dye which when coupled to a nucleic acid emits fluorescence and HPLC coupled with a fluorescence detector.

In accordance with the present invention there is provided a method for detecting in a sample the presence of intact viral particles containing nucleic acids, said method comprising the step of labeling said nucleic acids from said particles with a dye, said dye when complexed with said nucleic acids emitting fluorescence, and subsequently detecting by chromatography (such as without limitation ion exchange chromatography) a fluorescent eluted sample containing the labeled nucleic acids.

Still in accordance with the present invention, there is also provided a method for quantifying viral particles in a sample, said method comprising the step of:

i) contacting a viral lysate with Benzonase, under suitable conditions for digestion of the lysate by benzonase;
ii) labeling nucleic acids from said lysate with a dye, said dye once complexed with the nucleic acid emits fluorescence;
iii) subsequently eluting by chromatography (such as for example ion exchange chromatography) a fluorescent sample and producing an elution profile containing an elution curve for said fluorescent sample; and
iv) integrating the area under the elution curve for said fluorescent sample to obtain an integration value and comparing said integration value for said fluorescent sample with an integration value of a standard viral sample to obtain by extrapolation a concentration for said viral particles.

In one embodiment of the invention, the methods described above further comprise before the step of labeling, a step of purifying or semi-purifying said particles containing the nucleic acids.

Such semi-purification or purification can be carried on for example with CsCl gradient, iodixanol gradient, size exclusion chromatography or sucrose gradient.

The nucleic acids can be for example DNA, RNA, ssDNA or dsDNA.

In the embodiments of the methods of the present invention, the viral particles are preferably selected from the group consisting of adenovirus type 5, helper dependent adenovirus type 5, adeno-associated virus type 2, baculovirus and retroviral vectors.

In one embodiment, the dye is one from the class of asymmetrical and unsymmetrical dimeric and monomeric cyanine dyes, such as, without limitations, nucleic acid gel stains (e.g. SYBR® Gold, SYBR® Green I, SYBR® Green II (Molecular Probes, Eugene, Oreg.)), dimeric cyanine nucleic acid stains (e.g. thiazole orange dimer)(TOTO®), oxazole yellow dimer (YOYO®) (Molecular Probes, Eugene, Oreg.)), or fluorescent nucleic acid stains (e.g. PicoGreen®, RiboGreen® (Molecular Probes, Eugene, Oreg.)). The preferred dyes are SYBR® Gold and SYBR® Green I.

The motivation behind the idea of labeling the viral genome was in fact a problem of insensitivity of the IE-HPLC assays that are currently used to monitor viral particles such as RV and gutless AdV5 that are produced in low titers. The initial experiments conducted in this study was to determine if in fact the dye have the ability to access the genome traversing through the membrane (as in the case of the enveloped viruses) and the viral capsid. Virus detection and quantification using SYBR Green I and flow cytometry have been reported [Shen C F, et al., *J Virol Methods*. 2002; 105: 321-330; Brussaard C P, et al., *Appl Environ Microbiol*. 1999; 65: 45-52; Marie D, et al., *Appl Environ Microbiol*. 1999; 65(1): 45-52; and Brussaard C P., *J Virol Methods*. 2000; 85: 175-82] and most recently, the binding of RiboGreen to the genome of an intact human rhinovirus has been demonstrated [Kremser L, et al., *Anal Chem*. 2004; 76: 882-887].

Figure 8:
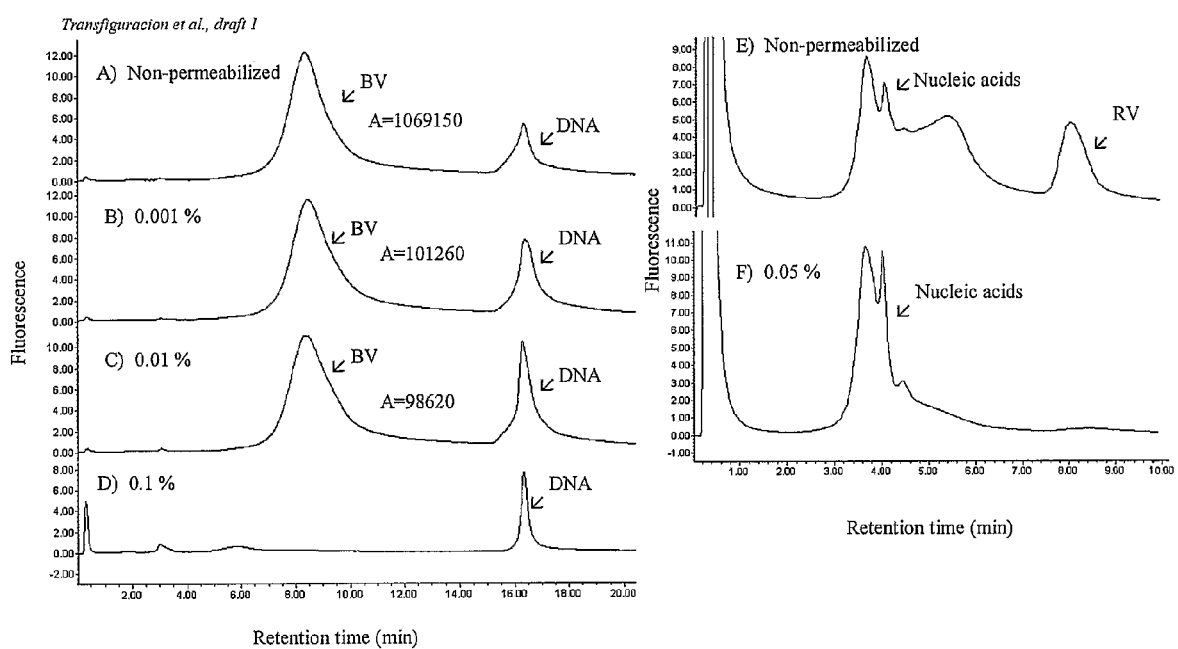
FIG. 8 illustrates HPLC elution profiles of non-permeabilized sucrose gradient purified labeled BV (FIG. 8A), and sucrose gradient purified labeled BV permeabilized with 0.001% Triton X-100™ (FIG. 8B), 0.01% (FIG. 8C), 0.1% (FIG. 8D) and non-permeabilized RV samples (FIG. 8E)
Figure 9A:
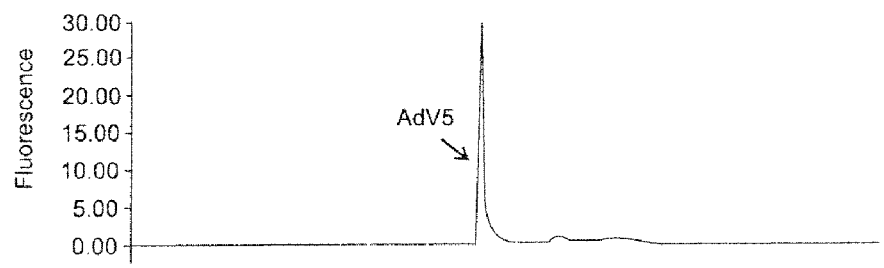
Figure 9B:
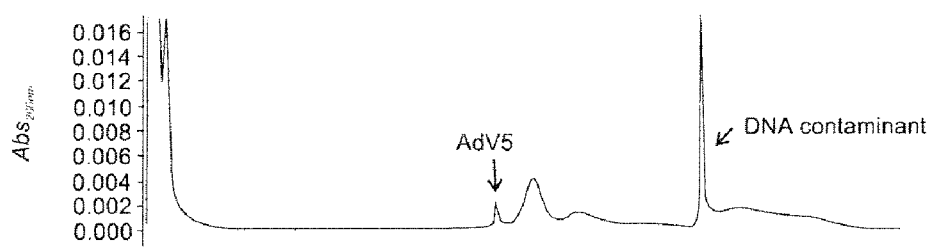
Figure 9C:
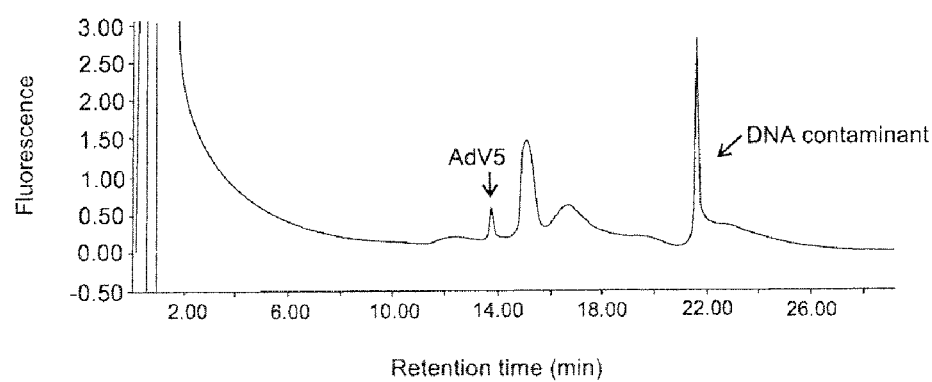
Figure 11A:
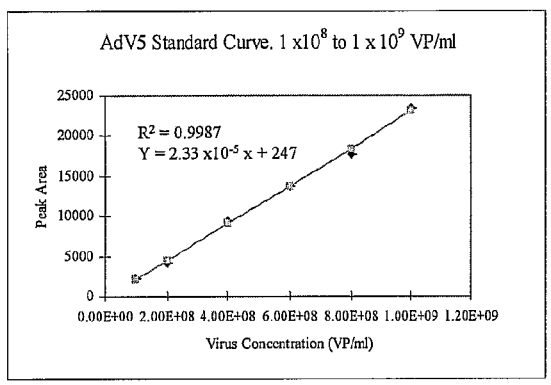
Figure 11B:
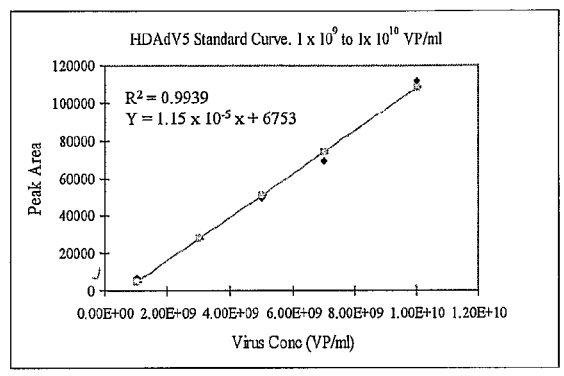

concentrated by ultracentrifugation in 20% sucrose cushion and semi-purified or permeabilized with 0.05% Triton X-100 (FIG. 8F);

FIG. 9 illustrates HPLC elution profiles of 1×CsCl purified AdV5 (FIG. 9A) of 1×AdV5 lysate without genome labeling detected by Abs260 nm (FIG. 9B) and of 1×AdV5 lysate labelled With 10-4 SYBR® Gold (FIG. 9C);

FIG. 10 illustrates HPLC elution profiles of a 1× non-benzonase digested (FIG. 10A) or benzonase digested (FIG. 10B) HDAdV5 lysate, the supposed elution time of the virus in the non-digested sample and the virus peak in the digested sample being indicated by an arrow; and FIG. 11 illustrates the working range linearity of AdV5 (FIG. 11A) and HDAdV5 (FIG. 11B) curves.

DETAILED DESCRIPTION OF THE PREFERRED EMBODIMENT

In accordance with the present invention, there is now provided a new method for the detection of viral particles by combining a two-step approach; first, the genome of the intact virus is labeled with a fluorescent dye followed by separation using IEX-HPLC equipped with a fluorescence detector. The method was further developed to quantify Ad type 5 (AdV5) and the helper dependent adenovirus type 5 particles to demonstrate its feasibility as a quantification assay. The inventors exploited the idea of labeling the genome of the intact virus since it has been shown that nucleic acids when complexed with a fluorescent dye exhibit maximum and excitation wavelengths resulting in the enhancement of sensitivity greater that 1000 fold [Tuma R S, et al., Anal Biochem. 1999; 268: 278-288]. The binding modes, sequence specificity and stability of these dyes with free double stranded (ds) and single stranded (ss) DNA in a solution have been investigated [Zipper H, et al., Nucleic Acids Res. 2004; 32: e103; Rye H S, et al., Nucleic Acids Res. 1992; 20: 2803-2812; Rye H S, Glazer A N. Nucleic Acids Res. 1995; 23: 1215-1222; and Geron-Landre B, et al., Nucleic Acids Res. 2003; 31: e125]. More recently, the binding of RiboGreeen to genomic RNA of an intact human rhinovirus was demonstrated without changing the native conformation of the virus [Kremser L, et al., Anal Chem. 2004; 76: 882-887; and Kremser L, et al., Anal Chem. 2004; 76: 7360-7365]. In the present invention, the inventors have used five viral vectors, two of which belong to the class of non-enveloped (capsid) virus, the AdV, HDAdV and MV, and two belonging to the class of enveloped viruses, the RV and BV, respectively.

Materials and Methods

Viral Vectors, Production and Purification

Five viral vectors (from the four different types described above) were used in this application. (i) AdV5, first generation (E1 deleted) encoding the green fluorescent protein (GFP) was produced in 293 cells [Cote J, et al., Biotechnol Bioeng. 1998; 59: 567-575] and purified by CsCl gradient [Graham F L, Prevec L. Mol Biotechnol. 1995; 3: 207-220]. AdV are icosahedral in shape with diameter between 65-80 nm and linear ds DNA genome size between 30-40 kb. (ii) HdAdV5 encoding the B-galactosidase gene was produced in 293 cells using AdV as the helper virus and purified by CsCl gradient (Umana et al., Nat. Biotechnol. 19: 582-585, 2001). (iii) Vesicular stomatitis virus-G glycoprotein (VSV-G) pseudotyped Moloney murine leukemia virus (Mo-MuLV) derived RV encoding the fusion of thymidine kinase (TK) and GFP [Paquin A, et al., Hum Gene Ther. 2001; 12: 13-23] produced in 293 suspension cells [Ghani K, et al., Large-scale production of retroviral vectors with suspension adapted 293 GPG cells. 2003. 6th Conference on Protein Expression in Animal Cells. September 7-11. Mont Tremblant, Que., Canada] and purified by size exclusion chromatography (SEC) [Transfiguracion J, et al., Hum Gene Ther. 2003; 14: 1139-1153]. RV is spherical in shape with diameter between 80-100 nm and has ss RNA genome of ~8 kb. (iv) AAV type 2 (MV2) that encodes GFP was produced in sf9 cells by co-infection of three baculovirus vectors and purified by a combination of cation, size exclusion and hydrophobic interaction chromatography and final step of iodixanol gradient purification according to a method described by Zolotukhin [Zolotukhin S, et al., Gene Ther. 1999; 6: 973-985]. MV are isometric in shape with diameters between 18-26 nm and have ss DNA genome of ~4.7 kb. BV carrying the cytomegalovirus (CMV) mammalian promoter encoding GFP was produced in sf9 cells and purified by sucrose gradient density ultracentrifugation [O'Reilly, D. R., et al., 1992. Baculovirus expression vectors: a laboratory manual. Oxford University Press, Oxford, United Kingdom]. (v) BV is rod in shape, 200-450 nm long and has ds DNA genome of ~130 kb.

Relative Purity Determination by SDS-PAGE

The virus purity of each virus studied was determined by SDS-PAGE under reducing conditions and silver staining using 4-15% Tris-Cl ready gels (BioRad Lab, Hercules, Calif.) according to manufacturer's instruction.

Infectious Viral Particles Determination of the Purified Vectors

The infectious viral particles per ml (IVP/ml) of the purified vectors was determined as follows: for AdV5 and AAV2, FACS analysis for the expression of the GFP reporter gene using 293E cells, for HDAdV5, the colorimetric assay for the detection of blue forming units using 293 cells was used, for RV, the FACS assay for the determination of GFP expression using 143B tumor cells was used and the plaque assay using 293E cells was used for BacMam, respectively. The brief description of the methods used can be found in the prior art [Cote J, et al., Biotechnol Bioeng. 1998; 59: 567-575; and Transfiguracion J, et al., Hum Gene Ther. 2003; 14: 1139-1153], incorporated herein in their entirety by reference.

Total Viral Particles Determination for AdV5 and HDADV5

The total viral particles per ml (TVP/ml) for AdV5 and HDAdV5 were performed using the PicoGreen® Assay (Murakami and McCaman, Analytical Biochem. 274: 283-288, 1999) with slight modification. Briefly, the purified virus samples were diluted in TE, pH 7.5, digested with 100 U/ml of Benzonase® (a genetically engineered endonuclease produced in E. coli; Merck KGaA, Darmstadt, Germany) for 30 min at RT, the viral capsid broken with the addition of 0.1% SDS incubated for 5 min at RT and the viral genome labeled with SYBR® Green I for 5 min prior to reading the fluorescence. Using a double stranded lambda DNA as standard, the DNA concentration of the unknown sample was calculated by the linear regression equation. The VP/ml based on the DNA concentration which is the genome of the vector is converted in VP/ml according to stoichiometric relationships. For AdV5 which has a dsDNA genome size of 35, 506 bp, 1 ng of genome is equivalent to $1.29 \times 10^{12}$ VP/ml. As for HDAdV5, which as a dsDNA genome size of 32, 600 bp, 1 ng of genome is equivalent to $2.80 \times 10^7$ VP/ml.

Fluorescent Dyes, RNA and DNA Standards

The nucleic acid stains used are the proprietary unsymmetrical cyanine dyes; SYBR® Gold and SYBR® Green I (Molecular Probes, Eugene, Oreg.). SYBR® Gold has specific binding to double stranded deoxyribonucleic acids (ds DNA) single stranded (ss) DNA and ribonucleic acids (RNA)

with an enhanced detection compared to UV (RNA) (Tuma R S, Anal. Biochem. 268: 278-288, 1999). SYBR® Gold/nucleic acid complex have maximum excitation and emission wavelengths at 495 and 537 nm, respectively. SYBR® Green I also has a specific binding to ds DNA with enhanced sensitivity as well as binding to ssDNA and RNA with a lesser degree of sensitivity (Zipper et al., Nucleic Acids Res., 32: e103, 2004). The maximum excitation and emission wavelengths of SYBR® Green I/nucleic acid complex are at 479 and 520 nm, respectively. Of course the person skilled in the art will understand that any nucleic acid stain that emits fluorescence once coupled to nucleic acids would be suitable to be used in the method of the present invention. The dye or stain by itself should not be fluorescent, or at least exhibit minimal fluorescence. The key when choosing an appropriate dye or stain is that the dye or stain allows for significant enhancement in signal when complexed with the genome (DNA or RNA) of the intact virus. DNA standard was a lambda ($\lambda$) ds DNA while RNA standard was a 16S and 23S ribosomal RNA from *E. coli* also from the same supplier as mentioned.

Samples Preparation and Viral Genome Labeling of Intact Virus

Prior to labeling, all samples were filtered through a 0.45 μm GHP Acrodisc™ membrane (Pall Life Sciences, Ann Arbor, Mich.). The fluorescent dye was thawed at room temperature (RT) and the manufacturer's instructions were followed. A $10^{-3}$ working solution (WS) of the dye was prepared by adding 1 μL of the stock ($10^4$) with 999 μL of 10 mM Tris, 1 mM ethylenediaminetetraacetic acid (EDTA), pH 8 (TE buffer). The genome labeling of the intact virus was performed by adding the appropriate volume of the WS to a final concentration of $10^{-4}$ to the virus sample then incubated at the specified temperature and time in the dark. The dilution of virus samples (when required) was performed with TE, pH 8 prior to labeling. AdV5, HDAdV5 and AAV2 were labeled with SYBR® Gold while RV and BacMam were labeled with SYBR® Green I, respectively. The intrinsic fluorescence characteristic of each of the viral vector studied was determined by analysis of non-labeled sample and detected by fluorescence at the maximum excitation and emission wavelengths of the dye (SYBR® Gold, SYBR® Green I)-nucleic acid complex described below.

In the present invention, other non-fluorescent dyes (but containing fluorophores) which could exhibit a strong signal upon complexing with nucleic acids are dyes from the class of asymmetrical and unsymmetrical dimeric and monomeric cyanine dyes such as thiazole orange dimer (TOTO®), oxazole yellow dimer (YOYO®), PicoGreen®, RiboGreen®, and SYBR® Green II, etc.

HPLC System

A HPLC Alliance system was used (Waters, Milford, Mass.) equipped with a 2690 separation module, in-line degasser, 996 photodiode array (PDA) and 2475 multi-wavelength fluorescence detectors and a Millennium32 software was used for data acquisition and peak integration.

HPLC Analysis

The columns used for analysis were UNOQ (anion) and UNOS (cation) polishing columns, 4.6×10 mm (Bio-Rad, Hercules, Calif.) for AdV5, HDAdV5, RV, BV and AAV2, respectively. The mobile phases used were: A) 0.25 M HEPES, pH 7.5, for AdV5, HDAdV5 and AAV2 and 0.1M Tris-Cl, pH 7.5 for RV and BacMam, respectively, B) 2 M and 1M NaCl in Milli Q Water for AdV5, HDAdV5 RV, BV and AAV2, respectively and C) Milli Q Water for all the vectors described. All solutions were filtered through a 0.45 μm membrane before use. Prior to sample injection, the column was always equilibrated with 5 column volumes (CV) of 20% A, 80% C and a buffer blank (50 mM HEPES, pH 7.5 for AdV5, HDAdV5 and AAV2 and 20 mM Tris-Cl, pH 7.5 for RV and BV, respectively) injected to ensure a flat baseline. The virus elution was performed as follows: Following sample injection and column wash, the virus eluted in a linear gradients from 300 to 600 mM NaCl in 20% for AdV5 and HDAdV5; from 500 to 1.1M NaCl in 20% A for RV, from 0 to 1 M NaCl in 20% A for BV and from 0 to 0.5 M in 20% A for AAV2. A two CV regeneration in NaCl concentrations of 600 mM, 1,1 M, 1 M and 500 mM for AdV5, RV, AAV2 and BV followed after elution and the column was re-equilibrated with 5 CV of 20% A, 80% prior to the next sample injection. A flow rate of 1 ml/min was used for all analysis except during the elution of AdV5 at 0.5 ml/min. The virus was detected simultaneously by Abs260 nm and 280 nm (Abs280 nm) and by fluorescence at maximum excitation and emission wavelengths of 495 and 537 nm for SYBR® Gold and 479 and 520 nm for SYBR® Green I, respectively.

AdV5 and HDAdV5 Total Virus Particles Quantification by Labeling the Viral Genome and Ion-Exchange HPLC i) Preparation of AdV5 and HDAdV5 Standard Curves for Quantification CsCl purified standards were quantified for their total viral particles concentration by the PicoGreen® Assay. The value obtained by this method was used as the reference concentration for the generation of the standard curve. To generate the curves, the standards were diluted in TE buffer pH 8 to cover the range from $1\times10^8$ to $1\times10^9$ VP/ml for AdV5 and $1\times10^9$ to $1\times10^{10}$ VP/ml for HDAdV5, respectively in a total volume of 300 μl. SYBR® Gold were then added at a final concentration of $10^{-4}$. Labeled virus standards were loaded onto the HPLC vial inserts, into the sample carousel and into the sample chamber previously equilibrated at 37° C. for AdV5 and 25° C. for HDAdV5. Buffer blank (50 mM HEPES, pH 7.5) were injected 2× before the first standard injection and thereafter every standard injection. Standards were injected in duplicate in volumes of 25 μl for AdV5 and 125 μl for HDAdV5. The standard curve is then generated by plotting the VP/ml in the axis against the peak area in the y-axis.

ii) Preparation of AdV5 and HDAdV5 Lysates and Quantification

AdV5 virus lysates were diluted 1/10 (as in the case of a 10× concentrated lysate) and labeled with SYBR® Gold at a final concentration of $10^{-4}$ for a maximum of 30 min in the dark prior to injection unto the column. For HDAdV5, the virus lysate was digested with Benzonase® for 30 min at RT prior to labeling with SYBR® Gold at a final concentration of $10^{-4}$. Sample injection volumes are described previously. The VP/ml concentration of the virus in the lysate was performed using the standard curve as described previously using the linear regression equation.

Results

Relative Purity of Purified Vectors

Figure 1:
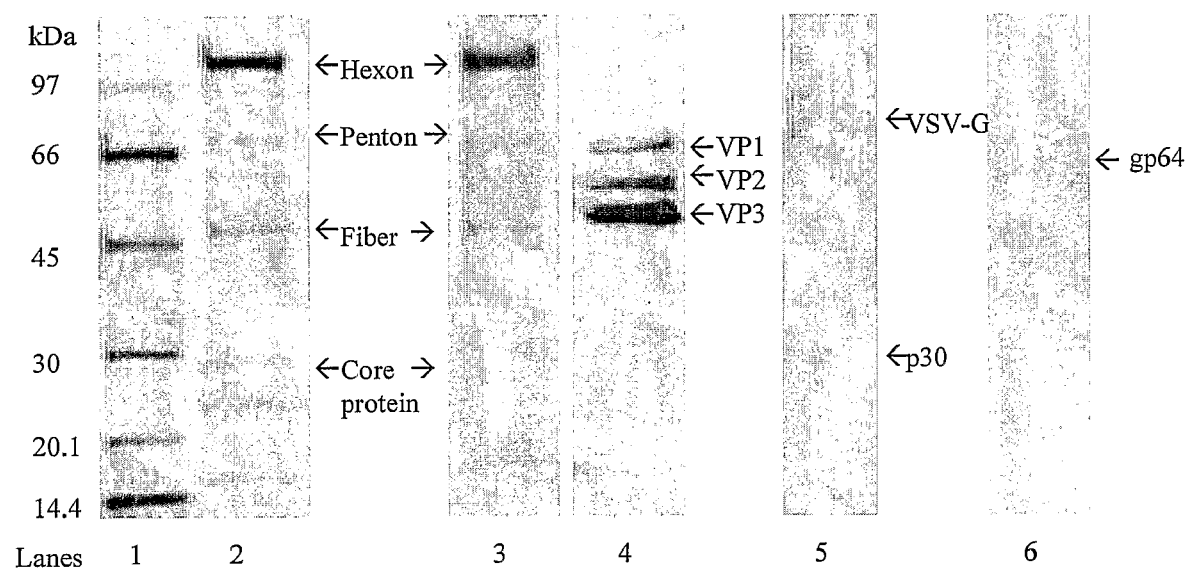
FIG. 1 illustrates SDS-PAGE (Silver stained) on 4-15% Tris-Cl reducing gels of highly purified viral vectors.

In-house standards were purified in-house and their relative purity was determined by SDS-PAGE with silver staining. For the development of this assay, it was necessary to have highly purified materials that are well characterized of their relative purity to identify the virus and rule out any possibilities of contaminant interferences. The relative purity of the vectors used in this study is shown in FIG. 1. By visual analysis, each of the viruses was highly purified with the detection of the major viral proteins and the virus envelope as in the case of the RV and BacMam. FIG. 1 illustrates a SDS-PAGE (Silver stained) on 4-15% Tris-Cl reducing gels of highly purified viral vectors. Lane 1 is low molecular weight protein markers, lane 2 is cesium chloride purified adenovirus type 5, lane 3 is cesium chloride purified helper dependent adenovirus type 5, lane 4 is iodixanol purified adeno-associated virus, lane 5 is size exclusion chromatography purified VSVG-G pseudotyped retroviral vector and lane six is sucrose gradient purified baculovirus vector carrying the mammalian promoter (BacMam). The major protein components and the virus envelope as in the case of retrovirus and BacMam are indicated by arrows.

Infectious Viral Particles of Purified Vectors

The IVP/ml for the purified vectors were as follows: $4.70\times10^{11}$ for AdV5, $3.58\times10^{10}$ for HDAdV5, $2.60\times10^9$ for AAV2, $1\times10^{10}$ for BacMam and $1.60\times10^7$ for RV.

Total Viral Particles Quantification

The total viral particles (TVP) quantification of AdV5 and HDAdV5 was performed using the PicoGreen® Assay. The results are $7.08\times1011$ TVP/ml for AdV5 and $3.58\times1010$ TVP/ml for HDAdV5. It was noticeable that the values obtained here were not significantly different from the values obtained with IVP/ml. For the purpose of quantification using the developed HPLC assay, the value obtained with this assay would be more suitable to use as a reference concentration since the encapsidated viral genome is specifically quantified rather than using the absorbance at 260 nm where the presence of residual DNA could contribute to the overestimation of viral particles in addition to the viral proteins which also absorb at 260 nm. In fact when the VP/ml of the purified AdV5 was quantified using the absorbance at 260 nm, the value obtained which was at $3.52\times1012$ VP/ml was significantly higher than the IVP/ml supporting the previous statement. The RV had a TVP/ml of $9.18\times108$ determined by NSEM. The TVP/ml for AAV2 was not determined because of the presence of 40% iodixanol in the solution which interferes with the Abs260 nm method. The TVP/ml for BV was $9.14\times1010$ determined by FACS analysis.

Figure 2A:
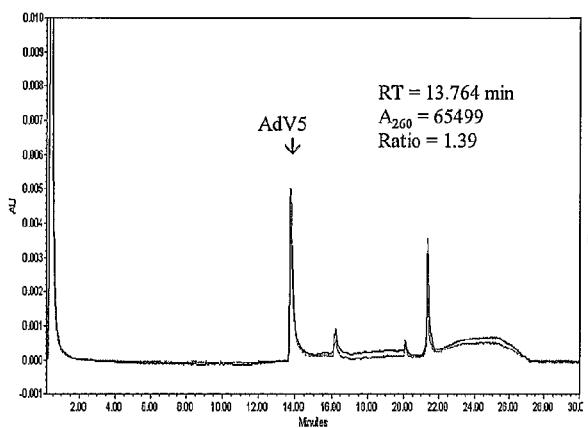
FIG. 2 illustrates HPLC elution profiles of adenovirus type 5 (AdV5) with an infectious virus particles concentration of $4.7 \times 10^{11}$ per ml non-labeled (FIG. 2A), detected by absorbance at 260 and 280 nm, and SYBR Gold labeled (FIG. 2B), detected by fluorescence, the virus peak before and after labeling being indicated by an arrow.
Figure 2B:
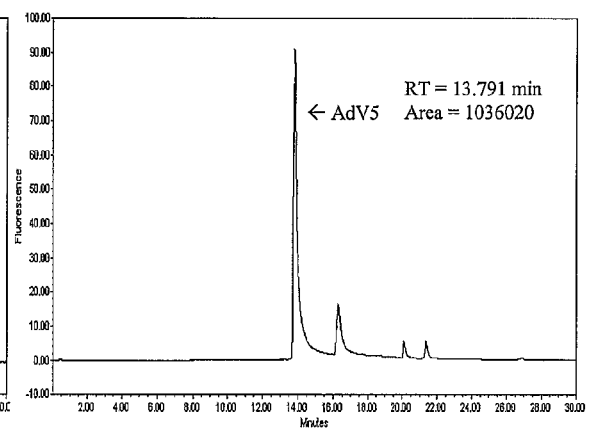
Figure 3A:
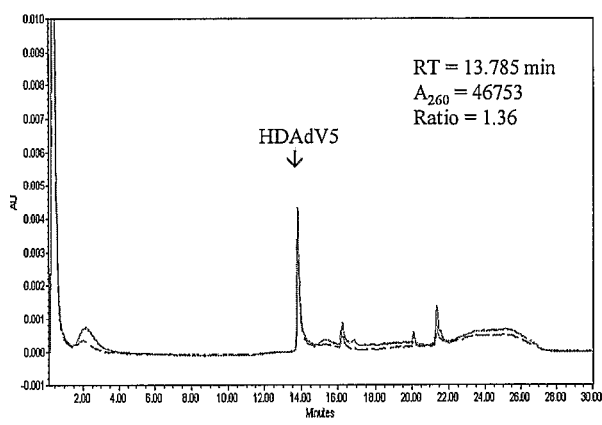
FIG. 3 illustrates HPLC elution profiles of helper dependent adenovirus type 5 (HDAdV5) with an infectious virus particles concentration of $2 \times 10^{10}$ per ml non-labeled (FIG. 3A), detected by absorbance at 260 and 280 nm, and SYBR Gold labeled (FIG. 3B), detected by fluorescence, the virus peak before and after labeling being indicated by an arrow.
Figure 3B:
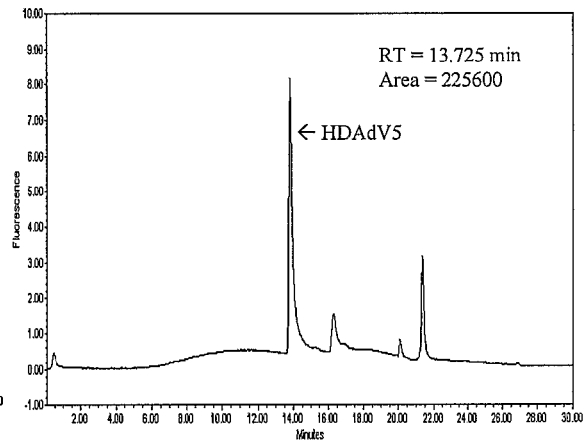
Figure 4A:
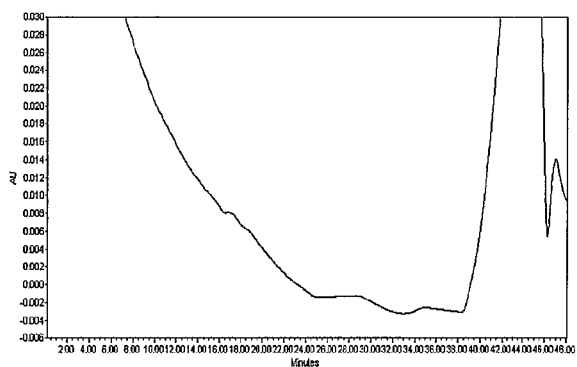
FIG. 4 illustrates HPLC elution profiles of an iodixanol purified adeno-associated virus type 2 (AAV2) with an infectious viral particles concentration of 2.60×109 per ml non-labeled (FIG. 4A), detected by absorbance at 260 nm, and SYBR® Gold labeled (FIG. 4B) detected by fluorescence, the virus peak after labeling being indicated by an arrow.
Figure 4B:
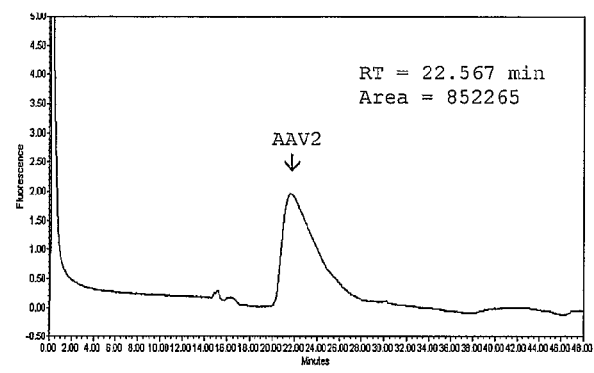
Figure 5A:
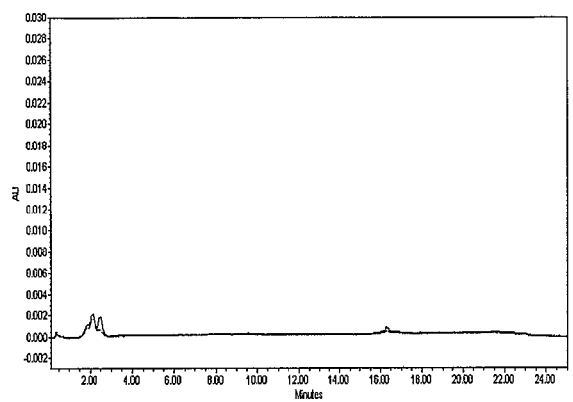
FIG. 5 illustrates HPLC elution profiles of sucrose gradient purified BacMam with an infectious viral particles concentration of 1×1010 per ml non-labeled (FIG. 5A), detected by absorbance at 260 nm, and SYBR® Green I labeled (FIG. 5B) detected by fluorescence, the virus peak after labeling being indicated by an arrow.
Figure 5B:
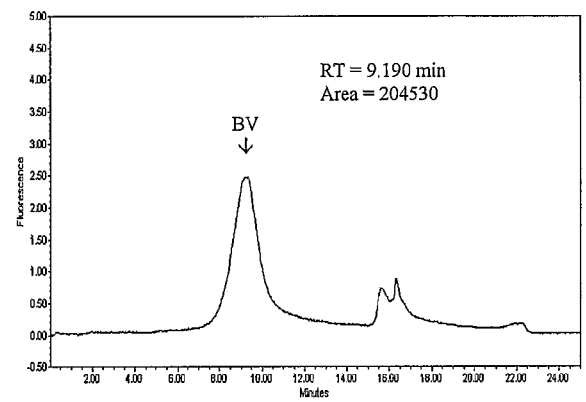
Figure 6A:
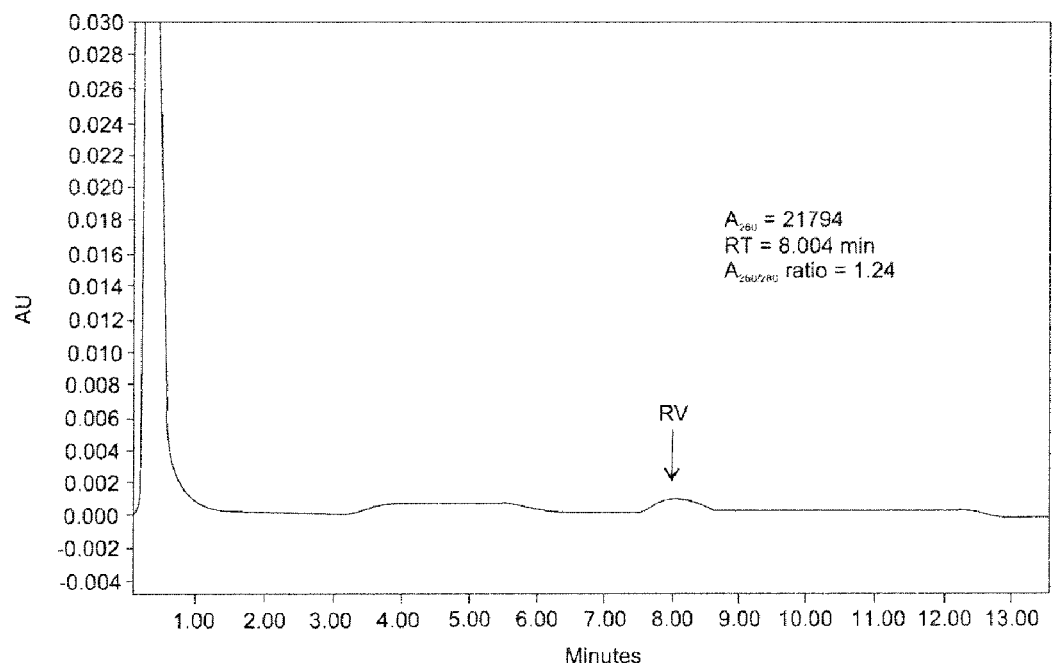
FIG. 6 illustrates HPLC elution profiles of a size exclusion chromatography purified retroviral vector with an infectious viral particles concentration of 1.33×107 per ml non-labeled (FIG. 6A), detected by absorbance at 260 nm and SYBR® Green I labeled (FIG. 6B), detected by fluorescence, the virus peak before and after labeling being indicated by an arrow.
Figure 6B:
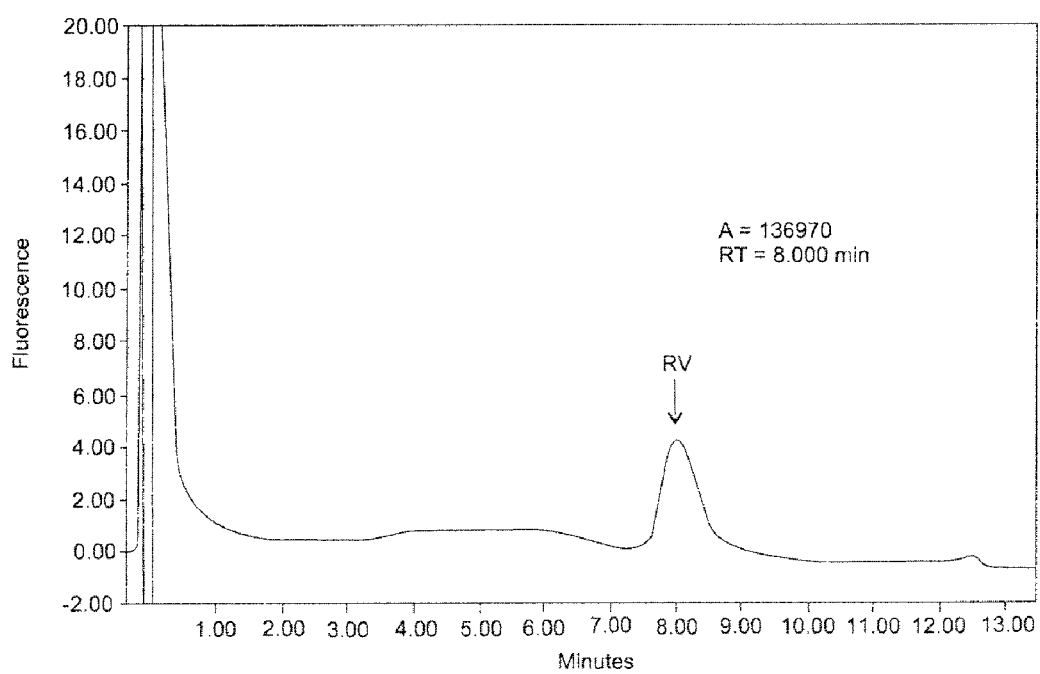

Genome Labeling of the Intact Vectors Significantly Enhanced the Peak Signal and Labeling Did not Indicate an Alteration in the Physical Properties of the Vectors The HPLC elution profiles of the vectors before and after labeling are shown in FIGS. 2-6. FIG. 2 illustrates the HPLC elution profile of AdV5 (4,7×1011 VP/ml) before and after labeling. The non-labeled virus (FIG. 2A) detected by absorbence (abs) at 260 nm (indicated by an arrow) was enhanced by ~94% upon labeling with SYBR® Gold (FIG. 2B) from peak area of 65499 to 1036020. The retention times of the virus before and after labeling were not significantly different at 13.785 min and 13.791 min, respectively. The other peaks detected after the virus elution were not identified except for the peak eluted at ~20 min which was a residual dsDNA (identified by a dsDNA std). The virus was eluted in ~480 mM of NaCl. FIG. 3 shows the HPLC elution profile of HDAdV5 (2×1010 VP/ml) before and after labeling. FIG. 3A is the non-labeled virus detected by abs at 260 nm while FIG. 3B is the SYBR® Gold labeled virus. The enhancement in sensitivity was ~79% upon labeling from peak area of 46753 to 225600. The retention times of both viruses did not differ significantly at 13.764 min and 13.725 min, respectively. Similarly as the AdV5 profiles, the other peaks detected were not identified except for the dsDNA eluted at ~20 min. The virus eluted in ~480 mM of NaCl. FIG. 4 shows the HPLC elution profiles of AAV2 (2,6×109 VP/ml) before and after labeling. The virus detected by abs at 260 nm (FIG. 4A) could not be identified because the presence of iodixanol which highly absorbs at 260 nm interfered with the detection. Upon labeling (FIG. 4B) with SYBR® Gold, the virus was clearly identified eluting in 22.567 min and at 230 mM of NaCl. FIG. 5 shows HPLC elution profiles of sucrose purified BacMam (1010 VP/ml) before and after labeling. The virus was not detected by abs at 260 nm (FIG. 5A) but was significantly detected upon labeling (FIG. 5B). The virus eluted in 9.190 min in 250 mM NaCl. The two peaks detected between 15 and 18 min were identified to be dsDNA peaks (by injection of a dsDNA std) FIG. 6 shows the HPLC elution profile of RV (1,33×107 VP/ml) before and after labeling. The virus peak upon labeling with SYBR® Green I was significantly enhanced by ~84% (FIG. 6B) compared to the non-labeled detected by abs at 260 nm (FIG. 6A). The retention times of both viruses did not vary at 8.004 and 8.000 min, respectively.

Intrinsic Fluorescence Signals

The intrinsic fluorescence signal of the vectors were determined by analysis of non-labeled samples and detected by fluorescence according to the specific excitation and emission wavelengths of the two fluorescent dyes used when coupled with nucleic acids. Peak areas obtained by HPLC indicated that the vectors have intrinsic fluorescent properties at the specified wavelengths but shown to be insignificant at <15% of the peak area obtained when the vectors were labeled.

Figure 7A:
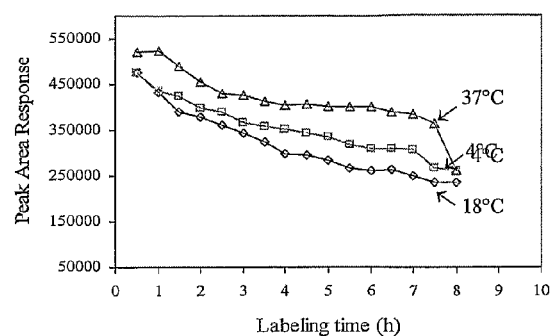
FIG. 7 illustrates efficiency of dye-genome complex formation as a function of time and temperature of a purified AdV5 (FIG. 7A) as a model for the non-enveloped viruses and purified BV (FIG. 7C) for the enveloped viruses, with the mean±sd of peak area responses of AdV5 from 2 to 7.5 h for the different temperatures (FIG. 7B) and the mean±sd of peak area responses of BV at different time range (FIG. 7D) when the response showed stability with the different temperatures investigated.
Figure 7C:
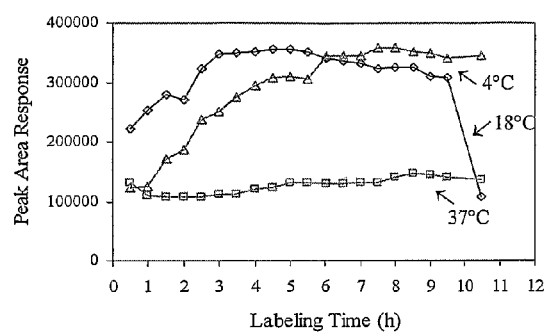
Figure 7B:
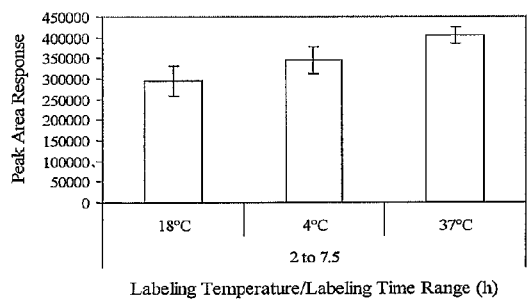
Figure 7D:
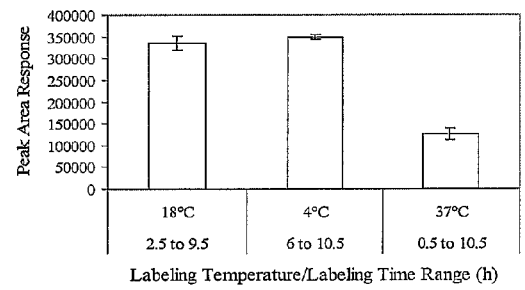

Dye-Viral Genome Complex Formation Efficiency is Dependent on Time and Temperature The effect of labeling time and temperature on the efficiency of the dye-genome complex formation in the intact virus was investigated. The formation of this complex with intact human rhinovirus (capsid virus) was reported to be dependent on time and temperature without changing the native conformation of the virus [Kremser L, et al., Anal Chem. 2004; 76: 882-887]. For the present invention, the AdV5 was used as a model for the non-enveloped viruses and BV for the enveloped viruses. The purified viruses, AdV5 and BV were diluted 1:100 in 50 mM HEPES, pH 7.5 and 1:10 in 20 mM Tris-Cl, pH 7.5, respectively. Subsequently, the diluted virus was labeled with $10^{-4}$ SYBR® Gold at 18° C., 4° C. and 37° C. At every 0.5 h interval, 25 µl of the labeled virus was injected onto the column for analysis. FIG. 7 shows the profiles of both viruses studied. FIG. 7A is the AdV5 labeled at 4° C., 18° C. and 37° C., respectively from 0.5 h until 8 h when the response started to decline. As can be seen, the responses obtained for all temperatures showed an identical trend, starting high at 0.5 h and linearly decreased until 7.5 h. A significant drop in the response was particularly observed with 37° C. at 8 h and a steady decline with 18° C. As shown, the 37° C. labeling temperature had the highest response followed by 4° C. and the lowest 18° C. In order to use this assay and be able to compare results at a variability <5%, the mean area responses were tabulated between 2 and 7.5 h of labeling (FIG. 7B). It was shown that the 37° C. mean response had less than 5% relative standard deviation (RSD) while the other two mean responses (18° C., 4° C.) had between 10 and 20% RSD. This means that with the assay's total analysis time of 23 min, 10 samples can be labeled at a time and injected consecutively expecting a 5% variation in the results obtained. FIG. 7C shows the peak area response of BV between 0.5 and 10.5 h, at 18° C., 4° C. and 37° C., respectively. In contrast to the results obtained with AdV5, the 18° C. had the highest response followed by 4° C. and 37° C. The pattern of dye-genome complex formation was also different from the AdV5 starting low at 0.5 h and increased linearly as observed with the 18° C. and 4° C. The response with 18° C. seemed to stabilize between 2.5 to 9.5 h showing a mean area response ±sd of 335780±16370 (FIG. 7D). The response obtained with 4° C. shows a slow and steady linear increase until 6 h then stabilizes until 10.5 h. The mean area response ±sd obtained between 6 to 10.5 h (348529±6051) for this temperature (FIG. 7D) was not significantly different from 18° C. Perhaps the most interesting results obtained were with 37° C. when the response did not show any change at all from 0.5 to 10.5 h of labeling. It seemed that there was a retardation of the dye-genome complex formation which could be assumed as restricted penetration of the dye to go through the envelope. A slow diffusion was observed with 4° C. showing a slow increase in the response before reaching maximum and saturation at 6 h of labeling. The mean response ±sd (12657±13090) obtained with 37° C. was significantly lower than the mean response obtained with 18° C. and 4° C. at time ranges when stability was achieved from 2.5 to 9.5 h, 6 to 10.5 and 0.5 to 10.5 h of labeling time. Both 18° C. and 4° C. are favourable temperature for labeling except that 4° C. was shown to be slower in reaching saturation.

Triton X-100 Permeabilization Does Not Increase the Virus Signal But Rather Destroys The Enveloped Viruses Several publications have indicated that membrane permeabilization of enveloped viruses increased the signal of the dye-genome complex [Shen C F, et al., J Virol Methods. 2002; 105: 321-330; Brussaard C P, et al., Appl Environ Microbiol. 1999; 65: 45-52; Marie D, et al., Appl Environ Microbiol. 1999; 65(1):45-52; and Brussaard C P., J Virol Methods. 2000; 85: 175-82]. In an attempt to increase the signal obtained with this assay, Triton X-100™ (non-ionic detergent) was used to permeabilize the envelopes of BV and RV prior to labeling and HPLC analysis. For the permeabilization of BV, different concentrations of Triton X-100; 0.001%, 0.01% and 0.1% were incubated with the virus sample for 5 min at 18° C. then labelled with $10^{-4}$ SYBR® Green I for 0.5 h in the dark at the same temperature. FIGS. 8A to 8D illustrate HPLC elution profiles of the non-permeabilized and permeabilized BV with 0.001%, 0.01% and 0.1% of Triton X-100, respectively. BV samples were purified on sucrose gradient. As shown by the peak area response, the non-permeabilized (FIG. 8A) and the 0.001% permeabilized BV (FIG. 8B) did not show any difference in the responses obtained. A slight decrease in the response was observed when the virus was permeabilized with 0.01% (FIG. 8C) while permeabilization with 0.1% completely destroyed the virus with the complete disappearance of the virus peak (FIG. 8D) and appearance of a more symmetrical dsDNA peak, a peak eluted in the flowthrough and a minor peak eluted at around 3 min. The last two peaks described were not detected with the other samples while the dsDNA contaminant peak did not show a symmetrical peak which is a typical characteristic of a pure dsDNA. The DNA signal obtained with this sample was largely contributed by the viral genome and the peaks eluted in the flowthrough and at around 3 min might be intrinsic fluorescence from the viral capsid or viral envelope with aromatic amino acids such as tryptophan and tyrosine. At least for the temperature used (18° C.) in the labeling, the membrane permeabilization did not increase the signal of the complex formation confirming a maximum saturation with the non-permeabilized virus. The permeabilization of RV with 0.05% Triton X-100 permeabilization was performed not so much to determine if there was an enhancement in the signal but to reconfirm the virus identity. The RV sample was concentrated by ultracentrifugation in 20% sucrose gradient cushion and semi-purified. Clearly and evidently, the virus peak completely disappeared upon treatment and an increased signal of the nucleic acids contaminants was also observed (FIGS. 8F and 8D) confirming the virus identity. Throughout FIGS. 8B to 8D and 8F, analysis was performed by permeabilization first then labelling with SYBR® Green I prior to HPLC separation.

Method Development for AdV5 and HDAdV5 Quantification Assay

Virus Lysate Labeling and Stability of Dye/Genome Complex in a Crude Preparation To demonstrate the feasibility of this detection method as a quantification assay AdV5 and HDAdV5 were used as models. The end goal of this was to use the method of the present invention as a quantification assay applicable in the analysis of low concentration of virus without the need of a pre-sample preparation. As previously stated, the AdV5 HPLC total particles quantification assay by UV detection [Klyushnichenko V, et al. J Chromatogr B Biomed Sci Appl. 2001; 755: 27-36; and Transfiguracion J, et al., J Chromatogr B Biomed Sci Appl. 2001; 761: 187-194] already in place in the inventor's laboratory is of limited sensitivity. For example, in the case of HDAdV, titer production is so low that in most cases it is at the limit of the assay detection. The general procedure used in such analysis of the lysate was to have a 10-fold concentrated virus to fall within the established working range of the assay [Transfiguracion J, et al., J Chromatogr B Biomed Sci Appl. 2001; 761: 187-194]. It was found that during labeling, the method in place was not applicable for the analysis of labeled virus lysates because of the presence of host residual DNA (that can also be strongly labeled) and other contaminants that have intrinsic fluorescence at the specified wavelengths overlapping the virus peak. Therefore the method was modified so that the virus was well resolved from the rest of the protein components. It was also determined that a 1× lysate was possible to be analysed with this method instead of the 10× lysate. With the 10× lysate, although a stronger virus signal was obtained, it was not highly resolved from the adjacent peaks resulting in a non-reliable integration. FIG. 9B shows the profile of a non-labeled 1× lysate detected by Abs260 nm and FIG. 9C shows the profile of a 1×SYBR® Gold labeled (10-4, 1 h @ 37° C.) lysate. The sample injection volume for both samples were 25 µl. FIG. 9A is a CsCl purified AdV5 to confirm the virus identity. In FIGS. 9A to 9C, the lysate was labeled for 1 h at 37° C. and analysed in a UNOQ Pol column, 0.16 ml. The virus in the lysate (indicated by an arrow) which has an IVP/ml of around 108 eluted at 13.69 min in 20 mM HEPES, pH 7.5+500 mM NaCl (FIG. 9B) efficiently resolved from the rest of the sample components. The stability of the dye-genome complex formation with this crude preparation was tested at 37° C., $10^{-4}$ SYBR® Gold and it was found that the response was not the same as the AdV5 purified material. The response started to be high at 0.5 h until 2.5 h of labeling with a relative standard deviation (RSD) of 5% then slowly declined with mean area response of between 10% and 20% RSD until 6 h of labelling. Somehow the rate of decay of the complex in this sample was faster (2 h) than with the purified material (5.5 h). This could be explained by the fact that in this preparation there is the presence of various contaminants that act as 9 fluorescence quenchers. In this case, four lysate samples could only be labelled at a time and injected consecutively expecting a 5% variation in the results obtained. In the case of HDAdV5 lysate, it was found that the profile was completely different from the AdV5. The digestion of the lysate with Benzonase® prior to analysis was necessary because the virus peak was indistinguishable. As shown with the non-Benzonase® digested lysate (FIG. 10A), the virus was not resolved from the adjacent peak. The supposed retention time of the virus in this profile is indicated by an arrow. Upon digestion with Benzonase®, the virus which was not previously resolved can now be distinguished and integratable (FIG. 10B).

Linearity Curve for the Working Range

The linearity of the curve for the established working range for the AdV5 and HDAdV5 was performed using the purified standards and shown in FIGS. 11A and 11B. As previously discussed, the reference concentrations used to generate the standard curve for quantification were those obtained by the PicoGreen® assay. FIG. 11A shows the curve for AdV5 with a correlation coefficient ($R2$) of 0.9987 for a working range between $1 \times 108$ and $1 \times 109$ VP/ml. The slope of the curve was $2.33 \times 10-5$ with a standard error of $5.80 \times 10-7$ and the intercept was 247 with a standard error of 352.29. While for HDAdV5 (FIG. 11B), the R2 obtained was 0.9939 for a working range between $1 \times 109$ to $1 \times 1010$ VP/ml. The slope of the curve was $1.15 \times 10-5$ with a standard error of $5.16 \times 10-7$ and the intercept was 6753 with a standard error of 3129.06.

Detection Limit (DL) and Quantification Limit (QL)

The DL and QL of the AdV5 and HDAdV5 assay were determined based on the standard deviation of the response of the three lowest concentration of the working range and the slope of the curve. The assay noise is determined and the DL is calculated as 3× assay noise and QL as 10× assay noise. Table 1 presents the results. The DL and QL for AdV5 are $2.55 \times 10^6$ and $8.50 \times 10^6$, respectively. While for HDAdV5 are $2.05 \times 10^7$ and $6.22 \times 10^7$, respectively.

TABLE 1

Detection Limit and Quantification Limit of ADV5 and HDAdV5 Viral Particles Quantification Assay by Labeling the Viral Genome and Ion Exchange HPLC

| | AdV5 | | HDAdV5 | | |
|---|---|---|---|---|---|
| Std Concentration (VP/ml) | Mean | SD | Std Concentration (VP/ml) | Mean | SD |
| $1 \times 10^8$ | 2212 | 4 | $1 \times 10^9$ | 6428 | 46 |
| $2 \times 10^8$ | 4191 | 44 | $3 \times 10^9$ | 28473 | 180 |
| $4 \times 10^8$ | 9388 | 25 | $5 \times 10^9$ | 49480 | 156 |
| Overall SD | | 19.80 | | | 71.50 |
| Slope of Curve | $2.33 \times 10^{-5}$ | | | $1.15 \times 10^{-5}$ | |
| Assay Noise | $8.50 \times 10^5$ | | | $6.22 \times 10^6$ | |
| Detection Limit | $2.55 \times 10^6$ | | | $2.05 \times 10^7$ | |
| Quantification Limit | $8.50 \times 10^6$ | | | $6.22 \times 10^7$ | |

Discussions

The results presented herein showing significant enhancement in the virus peak signal upon labeling clearly suggested that the virus was able to penetrate the membrane and the capsid to bind and form a complex with the genome. This complex which was extensively studied with pure DNA and RNA standards was shown to enhance the signal by more than a 1000-fold due to the increased in quantum yields [Tuma R S, et al., Anal Biochem. 1999; 268: 278-288; and Cosa G, et al., Photochemistry and Photobiology. 2001; 73: 585-599]. It was not known what are the underlying parameters of mass transport of these dyes in the surrounding environment but it was expected that dye-genome complex formation increases with elevated temperature. The rate of decay shown in the profile was demonstrated to be a typical characteristic of most cyanine dyes when complexed with dsDNA [Cosa G, et al., Photochemistry and Photobiology. 2001; 73: 585-599]. It can be assumed that dye penetration is a diffusion and breathing controlled process dependent on time but not temperature for BV. Clearly, the 37° C. response obtained was significantly lower than the response obtained with 18° C. and 4° C. Time dependency was in fact demonstrated with 4° C. because the response started low but overtime, it reached a plateau which could indicate saturation. The rate of decay of the dye-BV genome complex had also a slower rate of decay than the AdV5. A plateau was seen for the 18° C. response before it dropped significantly (FIG. 4C) while for the 4° C., the response remained to be stable even until 10.5 h of labeling. It was observed that the degree of sensitivity obtained with AAV2 and RV was lesser compared to AdV5 and BV as indicated in the larger sample volumes injected and the fluorescence scale of the HPLC profiles. These results was in fact anticipated since the intercalation binding mode of the dye to ssDNA or ssRNA is flexible giving the dye to have a more degree of rotational freedom relating to a smaller signal [Zipper H, et al., Nucleic Acids Res. 2004; 32: e103] in contrast to dsDNA where intercalation is highly restricted resulting in a highly fluorescent complex. Another important results presented herein is the use of non-ionic detergent Triton X-100 to permeabilize the membrane to increase the virus signal. The results obtained here were in fact contradictory to most of the published reports on virus membrane permeabilization. At least for the concentrations used and labeling temperature of 18° C., no enhancement in sensitivity but only a decline in the response at 0.01% and complete virus destruction at 0.1% and 0.05% for BV and RV, respectively (FIG. 5) was seen. These results clearly indicated that this detection method could be further developed as a quantification method for viral vector particles. The fact that it labels the viral genome specifically regardless whether the genome is complete or not shows the potential to measure vector genomes reliably. The feasibility of this method as a quantification assay using AdV5 and HDAdV5 was demonstrated herein. To generate the curve, CsCl purified materials were quantified of their particle concentration was quantified by PicoGreen® Assay. The method that was initially developed was optimized to resolve the virus in the lysate efficiently from the rest of the sample components. It was also found that AdV5 lysate analysis was more efficient with 1× concentration instead of 10× due to the presence of highly labelled compounds such as residual host DNA and even protein contaminants that have intrinsic fluorescence at the specified excitation and emission wavelengths. In the case of the HDAdV5 lysate, the need of a Benzonase® digestion prior to analysis is necessary to efficiently resolve the virus from the adjacent peak. It seems that the lysate of the HDAdV5 has more nucleic acid contaminants than the AdV5 as shown with the lysate profiles.

The linearity curve for AdV5 between $1 \times 10^8$ and $1 \times 10^9$ VP/ml showed a good correlation coefficient ($R^2$) of 0.9987 as well as the HDAdV5 with a $R^2$ of 0.9939 between $1 \times 10^9$ to $1 \times 10^{10}$ VP/ml. The DL and QL of the AdV5 assay were $2.55 \times 10^6$ and $8.50 \times 10^6$, respectively, while for HDAdV5 the DL and QL were $2.05 \times 10^7$ and $6.22 \times 10^7$, respectively.

In summary, labeling the genome of intact viral vectors with a fluorescent dye followed by IE-HPLC equipped with a fluorescence detector showed a significantly enhanced virus signal compared to UV detection. The labeled intact viral vector was efficiently resolved from residual host DNA or RNA without affecting its physico-chemical characteristics. Labeling time and temperature was demonstrated to affect the formation of the dye-genome complex. The assay was further developed for the quantification of AdV5 and HDAdV5 particles. The virus in the lysate preparation was efficiently resolved. In the case of the HDAdV5 lysate, digestion with Benzonase® prior to analysis was necessary. The virus in the lysate was detectable at 1× concentration which would not have been possible with the conventional UV detection method. The DL and QL of the AdV5 assay was shown to be superior to the existing method of detection. While for the HDAdV5 assay, the DL and QL permit the quantification of samples at low concentration production expected with this vector. In addition, this assay to our current knowledge is the first physical assay to be published for the quantification of viral particles for this vector.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features hereinbefore set forth, and as follows in the scope of the appended claims.

What is claimed is:

1. A method for detecting in a sample the presence of intact viral particles containing nucleic acids, said method comprising the steps of labeling said nucleic acids from said particles with a dye, said dye fluorescing when complexed with said nucleic acids and stimulated by light; eluting by chromatography a fluorescent sample, the eluted fluorescent sample containing the labeled nucleic acids; and detecting the eluted fluorescent sample.

2. The method of claim 1, further comprising before the step of labeling, a step of purifying or partially purifying said viral particles.

3. The method of claim 2, wherein the step of purifying or partially purifying the viral particles is effected on CsCl gradient, iodixanol gradient, size exclusion chromatography or sucrose gradient.

4. The method of claim 1, wherein the nucleic acids are DNA.

5. The method of claim 1, wherein the nucleic acids are RNA.

6. The method of claim 1, wherein the nucleic acids are ssDNA.

7. The method of claim 1, wherein the nucleic acids are dsDNA.

8. The method of claim 1, wherein the viral particles are selected from the group consisting of adenovirus type 5, helper dependent adenovirus type 5, adeno-associated virus type 2, baculovirus and retroviral vectors.

9. The method of claim 1, wherein the chromatography is an ion exchange chromatography.

10. The method of claim 1, wherein the dye is one from the class of asymmetrical and unsymmetrical dimeric and monomeric cyanine dyes.

11. The method of claim 10, wherein the dye is selected from the group consisting of nucleic acid gel stains, dimeric cyanine nucleic acid stains, and fluorescent nucleic acid stains.

12. The method of claim 11, wherein the dye is a nucleic acid gel stain.

13. A method for quantifying intact viral particles in a sample, said method comprising the step of:
   i) labeling nucleic acids from a lysate of virally infected cells with a dye which when complexed with the nucleic acids emits fluorescence;
   ii) subsequently eluting by chromatography a fluorescent sample and producing an elution profile containing an elution curve for said fluorescent sample; and
   iii) integrating the area under the elution curve for said fluorescent sample to obtain an integration value and comparing said integration value for said fluorescent sample with an integration value of a standard viral sample to obtain by extrapolation a concentration for said viral particles.

14. The method of claim 13, further comprising a step of purifying or partially purifying said viral particles.

15. The method of claim 14, wherein the step of purifying or partially purifying the particles is effected on CsCl gradient, iodixanol gradient, size exclusion chromatography or sucrose gradient.

16. The method of claim 13, wherein the chromatography is an ion exchange chromatography.

17. The method of claim 13, wherein the dye is one from the class of asymmetrical and unsymmetrical dimeric and monomeric cyanine dyes.

18. The method of claim 17, wherein the dye is selected from the group consisting of nucleic acid gel stains, dimeric cyanine nucleic acid stains, and fluorescent nucleic acid stains.

19. The method of claim 18, wherein the dye is a nucleic acid gel stain.

20. The method of claim 13, wherein the lysate is from an adenovirus type 5, a helper dependent adenovirus type 5, an adeno-associated virus type 2, a baculovirus or a retroviral vector.

21. The method of claim 13, wherein the nucleic acids are DNA.

22. The method of claim 13, wherein the nucleic acids are RNA.

23. The method of claim 13, wherein the nucleic acids are ssDNA.

24. The method of claim 13, wherein the nucleic acids are dsDNA.

* * * * *